United States Patent [19]

Bhakoo

[11] Patent Number: 5,629,282

[45] Date of Patent: May 13, 1997

US005629282A

[54] ANTIBACTERIAL COMPOSITIONS

[75] Inventor: Manmohan Bhakoo, Merseyside, Great Britain

[73] Assignee: Lever Brothers Company, Division of Conopco, Inc., New York, N.Y.

[21] Appl. No.: 317,275

[22] Filed: Oct. 4, 1994

[30] Foreign Application Priority Data

Oct. 5, 1993 [GB] United Kingdom ............... 9320443
Dec. 17, 1993 [GB] United Kingdom ............... 9325839

[51] Int. Cl.$^6$ .................. A23L 3/349; A23L 3/3499; A61K 38/16; A61L 2/18
[52] U.S. Cl. .................. 514/2; 134/25.3; 422/32; 424/54; 426/335; 426/532; 528/328; 530/300; 530/350
[58] Field of Search .................. 426/335, 532; 422/28, 32; 134/25.2, 25.3; 424/54; 528/327, 328; 514/2; 530/300, 350

[56] References Cited

U.S. PATENT DOCUMENTS

| | | | |
|---|---|---|---|
| 4,629,692 | 12/1986 | Dean | 530/389.8 |
| 5,204,099 | 4/1993 | Barbier et al. | 530/330 |
| 5,247,068 | 9/1993 | Donachy | 530/350 |
| 5,268,306 | 12/1993 | Berger et al. | 530/813 |

FOREIGN PATENT DOCUMENTS

| | | |
|---|---|---|
| 0149254 | 7/1985 | European Pat. Off. . |
| 0254419 | 1/1988 | European Pat. Off. . |
| 0510912 | 10/1992 | European Pat. Off. . |
| 2622195 | 4/1989 | France . |
| 168075 | 7/1991 | Japan . |
| 1237918 | 8/1967 | United Kingdom . |

OTHER PUBLICATIONS

Katchalski et al. (Nature, vol. 176, [4472], 16 Jul. 1965, pp. 118–119.
Shima et al. (Journal of Antibiotics, vol. XXXVII (1984) No. 11, pp. 1449–1455.
B. Davis (Surfactant Biocide Interactions), pp. 65–67 (not dated).
Philip Yeagle (The Structure of Biological Membranes), pp. 8–11, 396–399 (not dated).
G.D. Eytan (Techniques in the Life Sciences, vol. B4/1) pp. B416/1–B416/8 (1982).
Darnell et al. (Molecular Cell Biology (2nd Ed) Freeman and Co.) pp. 504–505 (not dated).
Methods in Enzymology, vol. 182 (1990) Acad Press, p. 516.
Santucci et al. (J. Med Chem, vol. 13[5], Sep. 1970), pp. 546–548.
Raj et al., (J. Biol Chem vol 265, No. 7 pp. 3898–3905 (1990).
Journal of Chemistry Society, Perkin I, pp. 538–546 (1981), Atherton et al, "Peptide Synthesis . . . ".
Chemical Abstracts 103:50279p (1985).
Biochemicals, Organic Compounds for research and for Diagnostic Reagents, published 1992 by Sigma Chemical Company, pp. 1742,1746, 1748–1749.
J. Biological Chemistry, vol. 189, issued 1951, Stahmann et al, "The Inhibition of Tobacco Mosaic Virus . . . ", pp. 45–52.
Translation of Japanese Kokai No. 3-168075 (Jul. 18, 1991).
Kirk–Othmer Encyclopedia of Chemical Technology, 3rd ed. New York: John Wiley & Sons, 1983, vol. 22, pp. 335, 363–365.

*Primary Examiner*—Jeffrey E. Russel
*Attorney, Agent, or Firm*—A. Kate Huffman

[57] ABSTRACT

The present invention relates to anti-bacterial compositions comprising particular compounds, to the use of the compounds as anti-bacterial agents, to the preparation of therapeutic or medicinal compositions comprising the compounds and to a method of disinfecting matter including the step of treating matter with the compounds. The compounds are identified as peptides having a molecular weight of at least 5 kD, comprising at least 15% by number of residues of arginine, lysine, ornithine or a mixture thereof and at least 15% by number of residues of arginine, lysine, ornithine, phenylalanine, tyrosine, tryptophan or a mixture thereof. Although the invention is described with reference to used in the fields of food and oral hygiene, the invention has particular utility in the field of household and/or industrial hygiene.

7 Claims, No Drawings

ANTIBACTERIAL COMPOSITIONS

FIELD OF THE INVENTION

The present invention relates to anti-bacterial compositions comprising particular compounds, to the use of said compounds as anti-bacterial agents, to the preparation of therapeutic or medicinal compositions comprising said compounds and to a method of disinfecting matter including the step of treating matter with said compounds. Although the invention is described with reference to used in the fields of food and oral hygiene, the invention has particular utility in the field of household and/or industrial hygiene.

BACKGROUND TO THE INVENTION

Peptides are polymers of amino acids. Amino acids are generally alpha-amino carboxylic acids, mostly with another functional group substituted at the alpha-carbon. Peptides can be synthesised by condensation of single types of, or mixtures of, amino acids.

Peptides which occur in nature differ greatly in molecular weight and properties but generally comprise polymers of varying numbers of around 20 naturally occurring, amino acid monomers. These are known as the 'standard' aminoacids, are generally of L-chirality and form peptides which have a highly structured sequence.

Random peptides can be synthesised in the laboratory with relative ease, whereas peptides with specific structured sequences require more complex synthetic methods. If it is desired that a synthetic peptide should simply have a structure which is not statistically random, this may be accomplished by modification of the molar ratio of amino acids present in the reaction mixture during the course of the synthesis.

For more highly structured peptides particular care must be taken to ensure that the reaction proceeds in discrete steps and this requires the use of either reaction-blocking agents or the so-called solid-phase synthesis, which employs a macroscopic substrate upon which peptides are grown and from which excess reagents can be washed. The nature of the reaction mixture may then be modified between each elongation step so as to ensure that specific sequences are produced.

For the purposes of the present specification the term 'pseudo-random' will be used to refer to both completely random peptides and to those in which no steps have been taken to inhibit or restrict peptide growth to single step elongation of the peptide chains so as to produce an ordered sequence of residues. These peptides, having far less structure than those found in nature, are known and have found applications as drug carriers or as reagents in immunological assay techniques.

Highly structured peptides, which have specific amino-acid sequences are known to engage in specific biochemical reactions. Examples of such peptides include hormones such as insulin and enzymes such as amylase, which have specific metabolic functions. Slight modification of the amino-acid sequence of these peptides can result in partial, if not complete, alteration of function.

It is known that certain highly structured peptides, which occur in nature, have an inhibitory or lytic activity when micro-organisms are exposed to them. Other peptides are known, such as certain snake-venom components, which exhibit similar activity towards the cells of higher plants or animals.

EP 510912 (Morinaga Milk) discloses antibacterial peptides which contain one or more of a specified set of amino acid sequences which are believed to be derived from the overall sequence of bovine lactoferrin and can be isolated by enzymic digestion of that protein. EP 510912 also relates to peptides which are produced by a method of synthesis, using an automated peptide synthesis technique generally following the method of Sheppard et al. (Journal of the Chemical Society Perkin I, p 538 1981) to produce specific peptides.

It is commonly supposed that the synthesis of moderately complex peptides by so-called 'genetic engineering' routes is a relatively simple task. However, despite considerable advances in recent years, the synthesis of specific peptides of a particular sequence on an industrial scale remains expensive and has been restricted to comparatively few peptides such as particularly valuable compounds of pharmacological interest and to certain enzymes. Thus, while structurally highly specific antimicrobial peptides are known they are expensive and difficult to produce.

The toxicity of antibacterial substances is conveniently expressed in terms of 'log-kills', e.g. a substance which reduces the viable count of cells in culture by 99.9% is effective at three log-kills, whereas a substance which reduces the viable count by a factor of 1 000 000 is effective at six log kills. For many applications of antibacterial substances 3–5 log kills is considered excellent performance. For dental pathogens, 2 log kills is considered adequate performance.

As will be apparent, the effectiveness of a particular antibacterial substance will be determined in part by the environment in which the substance acts and by the concentration of the substance. It should be noted that, particularly in bacterial populations, some cells may be resistant to the substance and effectiveness may not reach 100% (infinite log kills) even at high concentrations, whilst at much lower concentrations 3–5 log kills can still be achieved. Moreover, toxicity is expected to vary from one species of bacterium to another.

From the above it can be seen that, while some effective antibacterial peptides are known, they can be expected to be expensive to produce in relatively large quantities.

Antibacterial effects have been observed with simple peptides. In EP 0149254 (New York State University: 1985), poly L-histidine (of average molecular weight around 10000) is shown to have an antibacterial and fungicidal effect. It is believed that this effect is due to the structural similarity of these molecules to the naturally occurring histidine-rich peptides found in the mouth of humans and old-world monkeys.

EP 0254419 discloses that polylysine, especially that produced by the bacterium Streptomyces albus subsp (Dep 3834 FRI) has an antiviral activity.

GB 1237918 discloses that tetrapeptides of the general formula R-L-prolyl-L-leucyl-L-glycinamide and salts thereof, wherein R is an amino acid selected from glycine, tyrosine, leucine, tryptophan, serine, 3-hydroxypicolinic acid, asparagine, phenylalanine, proline, glutamic acid, arginine and histidine, express an antibacterial effect against a range of bacteria.

In order for antibacterial compounds to be used in products such as household cleaning compositions and household hygiene compositions they must be available at low cost, in quantity, and be effective at high log kills against a range of bacteria while present at relatively low levels.

BRIEF DESCRIPTION OF THE INVENTION

We have now determined that pseudo-random peptides which comprise one or more of arginine, lysine and ornithine exhibit surprisingly effective antibacterial properties against a broad range of bacteria and can consequently be obtained with relative ease and used in a wide range of applications. It is believed that these peptides are more effective as antibacterial agents than the poly-histidines known in the prior art.

The present invention is particularly concerned with pseudo-random peptides which achieve in excess of three log kills against bacterial cell populations when at peptide concentrations of as low as 0.1 mg/ml in a medium.

In particular, these peptides are those formed by random condensation of a mixture of amino acids comprising at least 15% by number of residues of arginine, lysine, ornithine or a mixture thereof and at least 15% by number of residues of arginine, lysine, ornithine, phenylalanine, tyrosine, tryptophan or a mixture thereof.

DETAILED DESCRIPTION OF THE INVENTION

A first aspect of the present invention subsists in the use as an antibacterial agent of a pseudo-random synthetic peptide, said peptide having a molecular weight of at least 5 kD and comprising at least 15% by number of residues of arginine, lysine, ornithine or a mixture thereof and at least 15% by number of residues of arginine, lysine, ornithine, phenylalanine, tyrosine, tryptophan or a mixture thereof.

According to a further aspect of the present invention there is provided a liquid or paste antibacterial composition comprising a pseudo-random synthetic peptide, said peptide having a molecular weight of at least 5 kD and comprising at least 15% by number of residues of arginine, lysine, ornithine or a mixture thereof and at least 15% by number of residues of arginine, lysine, ornithine, phenylalanine, tyrosine, tryptophan or a mixture thereof.

A further aspect of the present invention subsists in the use, in the preparation of a medicament or therapeutic composition for treatment of a bacterial disease, of a pseudo-random synthetic peptide, said peptide having a molecular weight of at least 5 kD and comprising at least 15% by number of residues of arginine, lysine, ornithine or a mixture thereof and at least 15% by number of residues of arginine, lysine, ornithine, phenylalanine, tyrosine, tryptophan or a mixture thereof.

A further aspect of the present invention subsists in a method for disinfecting matter, other than a method of therapy practised on the human or animal body which includes the step of treating said matter with an antibacterial pseudo-random synthetic peptide said peptide having a molecular weight of at least 5 kD and comprising at least 15% by number of residues of arginine, lysine, ornithine or a mixture thereof and at least 15% by number of residues of arginine, lysine, ornithine, phenylalanine, tyrosine, tryptophan or a mixture thereof.

As will be apparent from the background to the present invention, the pseudo-random peptides used in embodiments of the present invention, which were hitherto not suspected of having an antibacterial activity, can be obtained at relatively low cost. Moreover we have found that these peptides are surprisingly effective against a broad range of bacteria strains. Without the necessity for a precise sequence, the production costs of the peptides is greatly reduced as automated peptide synthesis and/or other biotechnological techniques such as genetic engineering of cellular sources are not required.

Peptides

Typically, the peptide comprises a co-polymer of at least one amino acid having an isoelectric point above 7 selected from arginine, lysine, ornithine or a mixture thereof and at least one amino acid having a bulky functional group selected from arginine, lysine, ornithine, phenylalanine, tyrosine, tryptophan or a mixture thereof.

We have determined that these pseudo-random peptides can achieve in excess of three log kills and in many cases in excess of six log kills when present at concentrations as low as 0.1 mg/ml. Without wishing to be restricted by any theory of operation it is believed that the presence of both basic and bulky amino acid residues is required for effective antibacterial activity, although the precise sequence of the residues is generally irrelevant. Bulky groups are those having a total of five or more carbons and heteroatoms. These include the aromatic groups derived from toluyl rings (as in phenylalanine and tyrosine) and indoles (as in tryptophan), as well as sufficiently long side chains such as the guanidine group of arginine, and the amino group of lysine.

While non-standard amino acids can be present in compositions according to the present invention, it is preferable, for reasons of availability, biodegradability and cost that the amino acids of the present invention should be those found in nature. These include ornithine, which is not an essential amino acid but does have a sufficiently high isoelectric point (close to 10).

It should be noted that arginine, lysine and ornithine have a sufficiently high isoelectric point and sufficiently bulky functional group in the side chain that their homopolymers, i.e. poly-arginine, poly-lysine and polyornithine are effective peptides in embodiments of the present invention.

Particularly preferred peptides are those which comprise homopolymers of arginine, lysine or ornithine and copolymers of lysine and phenylalanine, arginine and tryptophan and/or lysine and tryptophan. Mixed systems are also envisaged. One less preferred molecule is the copolymer of ornithine and tryptophan, as this appears to be active against a narrower range of bacteria.

All of the abovementioned amino acids are naturally occurring in the L chirality and consequently it is preferred that this form of the amino acid is used.

The molar ratio of amino acids of the two types is preferably 5:1–1:2 with an equal or predominant molar quantity of the basic amino acid being preferred.

Other amino acid residues can be present in the peptide. As illustrated by example below, serine and alanine can be present without reduction in the efficacy of the compositions. It is preferred that less than 50% of amino acids other than basic or aromatic amino acids are present in the peptide.

Peptides according to the present invention typically comprise up to 5000 amino acid residues, more preferably up to 3000 amino acid residues. Within these ranges, longer chains are believed to be more effective than shorter chains. We have found that peptides having a molecular weight of below 5 kD are much less effective as antibacterials.

Typical levels of peptide in liquid or paste products range from 0.001–10wt %, preferred levels being 0.01–1.0wt %. Effective concentrations of the peptide fall into the range 0.1–10 mg/ml, with concentrations of around 0.5–1 mg/ml being particularly preferred.

Haemolysis data for sheep erythrocytes show that the peptides of the present invention are not sufficiently haemolytic to be harmful to mammals under normal conditions of use.

The peptides of the present invention may be used in combination with other anti-microbial agents and treatments, such as antibiotics, high temperature and pressure. However it is preferred that treatments at elevated pressures and temperatures are avoided, particularly in household cleaning.

Surfactants

Surfactants are unessential components of compositions according to the present invention.

The surfactant is preferably nonionic, amphoteric, zwitterionic or cationic. Anionic surfactants, are less preferred as they are believed to interact with the peptides so as to prevent or reduce the antimicrobial activity of the peptides, particularly against Gram-negative bacteria.

The surfactant is preferably a non-ionic surfactant, an amphoteric surfactant or a mixture of the two.

Preferably the nonionic surfactant is an alkoxylated non-ionic surfactant. Ethoxylated nonionics are particularly preferred.

Preferably the amphoteric surfactant is a betaine.

Preferred surfactant levels range from 1–30% wt on composition.

Compositions

The most preferred embodiments of the invention comprise:

a) 0.001–2.0wt % of a peptide as described above,
b) 1–30wt % of a non-ionic surfactant,
c) as the balance of the composition, a compatible aqueous, liquid medium.

Particularly preferred antibacterial compositions comprise:

a) 0.001–0.1wt % of a peptide having a molecular weight of at least 5 kD, comprising at least 15% by number of residues of arginine, lysine, ornithine or a mixture thereof and at least 15% by number of residues of arginine, lysine, ornithine, phenylalanine, tyrosine, tryptophan or a mixture thereof
b) 1–30wt % of surfactant, said surfactant comprising an ethoxylated alcohol, a betaine or a mixture thereof, and,
c) as the balance of the composition, a compatible aqueous medium.

In addition to the abovementioned essential components, compositions according to the present invention may comprise further components selected with the use of the composition in mind and provided that these components are compatible with the peptides.

Uses of the compositions are preferably in household cleaning and hygiene compositions, although it is envisaged that the present invention may be embodied in products intended for application to the human skin, teeth or hair for cosmetic, washing or cleansing purposes. Such compositions include, but are not limited to personal washing bars, facial or body liquid cleaners, toothpastes, mouthwashes, antiperspirants and deodorants, shaving foams, creams and soaps, shower gels, cosmetics and shampoo products. The use of the compositions according to the invention in medicinal and therapeutic compositions is not intended to be excluded.

For embodiments of the invention not specifically described herein the effectiveness of any particular pseudo-random peptide against a specific type of cell can be determined by a comparison in the viable count between cell cultures incubated in the presence of the peptide and similar cell cultures incubated in the absence of the peptide. This is a relatively simple technique by use of which peptides suitable for a particular application can be identified. It is envisaged that some of the heteropolymers described herein will have antiviral, antimold or antifungal activity.

In order that the invention may be further understood it will be described hereinafter with reference to the following non-limiting examples.

EXAMPLES

The following examples illustrate the antimicrobial activity of compositions according to the preset invention with particular reference to activity against bacteria.

Materials used in the examples are identified as follows.

The peptides are identified in the table by their component amino acids given in standard notation in square brackets, and, where available, the ratio of these amino acids and the average molecular weight of the peptides. The majority of the peptides are either homopolymers of one amino acid or heteropolymers of two amino acids. All of these peptides are available from Sigma.

In some examples [Pro,Gly-Pro] is used. This peptide comprises repeating blocks of [L proline and L-glycine-L-proline] units, and is available as P6665 ex SIGMA.

In other examples the material identified as [Arg,Pro,Thr] is used. This material is a random polymer of arginine, proline and threonine in a ratio of 6:3:1. This material is available from Sigma.

Surfactants and other components present in the compositions of the examples are listed below.

| | |
|---|---|
| SDS | Sodium dodecyl sulphate, anionic detergent ex BDH. |
| TRITON | Triton X-100 ™, nonionic surfactant, ex BDH |
| Tween | Tween ™ 80 |

Example 1

Antimicrobial activity was determined by preparing compositions as given in tables 1–3 below in liquid media, incubating for two hours and thereafter determining total viable count/ml by plating-out samples in serial dilution onto nutrient agar (ex OXOID [TM]) and counting colonies formed after incubation of the agar plates both in the presence and in the absence of the peptide.

When present, the peptide was present at a concentration of 2.5 mg/ml. Toxicity results are presented as log deaths given initial bacterial concentrations of $2.5 \times 10^6$ to $2.3 \times 10^8$ viable cells/ml. Higher scores indicate more effective antimicrobial compositions, i.e. 5 is a $10^{-5}$ reduction in viable cell count.

For convenience, examples in which more than three log-kills were observed are marked in bold type.

TABLE 1

Toxicity to S. aureus

| Additive:<br>Peptide | none | SDS | TRITON | EDTA |
|---|---|---|---|---|
| EXAMPLES: | | | | |
| [Arg, Trp, 4:1] 31 kD | 4.48 | 2.97 | 4.48 | 1.66 |
| [Arg, Pro, Thr] 18 kD | 6.04 | — | — | — |
| [Lys, Trp, 4:1] 38 kD | 3.78 | 3.78 | 3.78 | 3.78 |
| [Lys, Phe, 1:1] 47.2 kD | 5.92 | 4.07 | 5.92 | 3.46 |
| [Arg, Arg] 8.9 kD | 3.03 | — | — | — |
| [Arg, Arg] 11.6 kD | 6.36 | 6.36 | 1.70 | 0 |
| [Arg, Arg] 43 kD | 6.40 | — | — | — |
| [Arg, Arg] 45 kD | 6.24 | — | — | — |
| [Arg, Arg] 139 kD | 6.40 | — | — | — |
| [Arg, Tyr, 4:1] 22 kD | 5.41 | — | — | — |
| [Arg, Ser, 3:1] 21.8 kD | 6.94 | — | — | — |
| [Orn, Orn] 14.5 kD | 6.40 | — | — | — |
| [Orn, Orn] 23.0 kD | 6.88 | — | — | — |
| [Orn, Orn] 46.0 kD | 6.88 | — | — | — |
| [Orn, Ser, 3:1] 22 kD | 6.88 | — | — | — |
| [Orn, Leu, 1:1] 35.0 kD | 6.74 | — | — | — |
| [Orn, Trp, 4:1] 31.0 kD | 0.12 | — | — | — |
| [Lys, Ala 2:1] 50 kD | 5.58 | — | — | — |
| [Lys, Ala 1:1] 41.6 kD | 5.48 | — | — | — |
| [Lys, Tyr, 1:1] 128 kD | 6.28 | — | — | — |
| [Lys, Tyr, 4:1] 24 kD | 6.28 | — | — | — |
| [Lys, Ser, 3:1] 32.2 kD | 4.73 | — | — | — |
| [Lys, Lys] 7.9 kD | 6.23 | — | — | — |
| [Lys, Lys] 8.0 kD | 6.49 | — | — | — |
| [Lys, Lys] 26.3 kD | 6.41 | — | — | — |
| [Lys, Lys] 51 kD | 6.41 | — | — | — |
| [Lys, Lys] 132.3 kD | 6.41 | — | — | — |
| [Lys, Lys] 224.5 kD | 4.60 | — | — | — |
| [Lys, Glu, 4:1] 198.2 kD | 4.72 | — | — | — |
| COMPARATIVE EXAMPLES: | | | | |
| [Pro, Gly-Pro] 5.3 kD | 0 | 3.41 | 0.34 | 0.75 |
| [Trp, Trp] 4 kD | 0 | 3.10 | 0.25 | 0.75 |
| [Tyr, Tyr] 27 kD | 0.76 | — | — | — |
| [Tyr, Glu, 1:1] 43.2 kD | 0.55 | — | — | — |
| [Pro, Pro] 8.0 kD | 0 | — | — | — |
| [Pro, Pro] 30 kD | 0.16 | 5.41 | — | — |
| [Ser, Ser] 5.6 kD | 0.40 | — | — | — |
| [His, His] 6.3 kD | 0.06 | — | — | — |
| [Lys, Trp, 1:9] | 0.36 | — | — | — |
| [Lys, Tyr, 1:9] 80 kD | 0.61 | — | — | — |
| [Lys, Lys] 3.97 kD | 0.42 | — | — | — |
| none | 0 | 0 | 0 | 0.22 |
| Tween 80 | 0 | — | — | — |

From the results given in table 1 it can be seen that compositions according to the present invention produce a marked reduction in the viable count of *S. aureus* in almost all circumstances whereas compositions in which other random peptides are present do not reduce the viable count except when the surfactant SDS is present. Surprisingly, while SDS might be believed to show an antimicrobial activity against *S. aureus*, and consequently a reduction in viable count in the presence of SDS would be expected, SDS alone does not reduce the viable count.

From the results it can be seen that the identity of the component amino acids in the peptides is of particular importance. Where arginine, orthithine or lysine are present as the only components, acceptable kill is generally attained. When these components are absent it is believed that an acceptable kill is not attained.

The results show that the relative ratio of the amino acids is of some significance. In examples using lysine and either tyrosine or tryptophan in a 1:9 ratio, less than 15% lysine is present in both cases and a low kill is observed. When the ratio is more balanced and the ratio of lysine to tyrosine or tryptophan is 1:1 or better 4:1 an acceptable kill is observed.

The results show that the size of the peptide is of some significance. In the examples using poly-lysine, a polymer with a molecular weight of 3.97 kD gave poor results whereas those polymers with molecular weights of 7.9–224.5 kD gave an acceptable kill. For the examples using poly-arginine it can be seen that against this strain borderline results were obtained with a molecular weight of 8.9 kD.

Some anomalous results are noted: while poly-ornithine gives acceptable results at both 23 and 46 kD. The ornithine/tryptotphan 4:1 co-polymer with a similar molecular weight (31 kD) gives poor results. However, as will be shown in later examples this co-polymer is effective against certain types of bacteria.

It is noted that [His,His] having a molecular weight of 6.3 kD shows a relatively low kill.

TABLE 2

| Toxicity to *E. coli* | | | | |
|---|---|---|---|---|
| Additive: Peptide | none | SDS | TRITON | EDTA |
| EXAMPLES: | | | | |
| [Arg, Trp, 4:1] 31 kD | 5.88 | 0.99 | 5.88 | 5.88 |
| [Arg, Pro, Thr] 18 kD | 6.20 | — | — | — |
| [Lys, Trp, 4:1] 38 kD | 4.54 | 0.93 | 4.54 | 4.54 |
| [Lys, Phe, 1:1] 47.2 kD | 6.34 | 0.20 | 6.34 | 6.34 |
| [Arg, Arg] 8.9 kD | 1.07 | — | — | — |
| [Arg, Arg] 11.6 kD | 6.68 | 0.32 | 6.68 | 4.40 |
| [Arg, Arg] 43 kD | 5.07 | — | — | — |
| [Arg, Arg] 45 kD | 6.59 | — | — | — |
| [Arg, Arg] 139 kD | 7.26 | — | — | — |
| [Arg, Tyr, 4:1] 22 kD | 6.56 | — | — | — |
| [Arg, Ser, 3:1] 21.8 kD | 6.76 | — | — | — |
| [Orn, Orn] 14.5 kD | 5.58 | — | — | — |
| [Orn, Orn] 23.0 kD | 6.13 | — | — | — |
| [Orn, Orn] 46.0 kD | 7.10 | — | — | — |
| [Orn, Ser, 3:1] 22 kD | 5.80 | — | — | — |
| [Orn, Leu, 1:1] 35.0 kD | 7.08 | — | — | — |
| [Orn, Trp, 4:1] 31.0 kD | 0.12 | — | — | — |
| [Lys, Ala 2:1] 50 kD | 6.36 | — | — | — |
| [Lys, Ala 1:1] 41.6 kD | 5.14 | — | — | — |
| [Lys, Tyr, 1:1] 128 kD | 6.61 | — | — | — |
| [Lys, Tyr, 4:1] 24 kD | 6.61 | — | — | — |
| [Lys, Ser, 3:1] 32.2 kD | 4.78 | — | — | — |
| [Lys, Lys] 7.9 kD | 6.43 | — | — | — |
| [Lys, Lys] 8.0 kD | 6.49 | — | — | — |
| [Lys, Lys] 26.3 kD | 4.86 | — | — | — |
| [Lys, Lys] 51 kD | 6.79 | — | — | — |
| [Lys, Lys] 132.3 kD | 5.45 | — | — | — |
| [Lys, Lys] 224.5 kD | 4.56 | — | — | — |
| [Lys, Glu, 4:1] 198.2 kD | 3.07 | — | — | — |
| COMPARATIVE EXAMPLES: | | | | |
| [Pro, Gly-Pro] 5.3 kD | 1.74 | 1.79 | 1.91 | 2.74 |
| [Trp, Trp] 4 kD | 0.50 | 0.00 | 0.42 | 0.68 |
| [Tyr, Tyr] 27 kD | 0.48 | — | — | — |
| [Tyr, Glu, 1:1] 43.2 kD | 0.44 | — | — | — |
| [Pro, Pro] 8.0 kD | 0.22 | 0.38 | — | — |
| [Pro, Pro] 30 kD | 0.16 | 5.41 | — | — |
| [Ser, Ser] 5.6 kD | 0.40 | — | — | — |
| [His, His] 6.3 kD | 1.15 | — | — | — |
| [Lys, Trp, 1:9] | 0.24 | — | — | — |
| [Lys, Tyr, 1:9] 80 kD | 0.62 | — | — | — |
| [Lys, Lys] 3.97 kD | 0.55 | — | — | — |
| none | 0 | 0.14 | 0 | 0 |
| Tween 80 | 0.06 | — | — | — |

From the results given in table 2 it can be seen that compositions according to the present invention produce a marked reduction in the viable count of *E. coli* in almost all circumstances whereas compositions in which other random peptides are present do not reduce the viable count. It can be seen that as with Table 1, when the surfactant SDS is present different performance is exhibited. It is believed that the peptide and SDS have a greater mutual affinity than that of either to *E. coli*, consequently no reduction in viable count in the presence of SDS would be expected.

The results in table 2 generally show the same effects due to molecular weight and ratio of components as do those of table 1. In table 2 it can be seen that poly-arginine with a molecular weight of 8.9 kD is much less effective against this strain that the higher molecular weight polyarginines. It can again be seen that while [His,His] is one of the better comparative examples the effects fall far short of those attained with the peptides of the present invention.

TABLE 3

Toxicity to *P. aeroginosa*

| Additive: Peptide | none | SDS | TRITON | EDTA |
|---|---|---|---|---|
| EXAMPLES: | | | | |
| [Arg, Trp] 31 kD | 4.98 | 0 | 4.98 | 4.98 |
| [Lys, Trp] 38 kD | 4.26 | 0 | 4.26 | 4.26 |
| [Lys, Phe] 47.2 kD | 5.78 | 0.07 | 5.78 | 5.78 |
| [Arg, Arg] 11.6 kD | 5.76 | 0 | 5.76 | 5.76 |
| [Orn, Trp] 31 kD | 5.64 | — | — | — |
| COMPARATIVE EXAMPLES: | | | | |
| [Pro, Gly-Pro] | 0.11 | 0 | 0.25 | 0.89 |
| [Pro, Pro] 8.0 kD | 0.21 | 0.39 | — | — |
| [His, His] 6.3 kD | 0.34 | — | — | — |
| None | 0 | 0 | 0 | — |
| Tween 80 | 0 | — | — | — |

From the results given in Table 3 it can be seen that compositions according to the present invention produce a marked reduction in the viable count of *P. aeroginosa* in almost all circumstances whereas compositions in which other random peptides are present do not reduce the viable count. It can be seen that as with Table 2, when the surfactant SDS is present different performance is exhibited. It is again believed that the peptides and SDS have a greater mutual affinity than that of either to *P. aeroginosa*, consequently no reduction in viable count in the presence of SDS would be expected.

It can also be seen that the heteropolymer of ornithine and tryptophan exhibits some activity against *P. aeroginosa*, whereas this polymer shows little or no activity against the micro-organisms mentioned in tables 1 and 2.

Example 2

Table 4 below shows the effect of varying the concentration of the poly-lysine (132.4 kD) and poly-arginine (139.2 kD) as regards the log kills obtained with these poly amino acids. In all cases the initial inoculum comprised $3.7 \times 10^8$ to $2.1 \times 10^9$ viable cells/ml and incubation was allowed to proceed for two hours at room temperature.

TABLE 4

Effect of Concentration

| Polyaminoacid Concentration (mg/ml) | LOG KILL | | | |
|---|---|---|---|---|
| | Polylysine | | Polyarginine | |
| | S. aureus | E. coli | S. aureus | E. coli |
| 2.5 | >7.00 | 5.94 | >6.91 | >7.38 |
| 1.25 | >7.00 | 4.63 | >6.91 | 5.73 |
| 0.625 | 7.00 | 3.67 | >6.91 | 6.85 |
| 0.312 | 6.60 | 3.20 | 4.36 | 2.18 |
| 0.156 | 5.15 | 2.10 | 1.57 | 0.63 |

Example 3

The abovementioned examples 1 and 2 relate to bacterial strains which are common household bacteria. In order to demonstrate the wider applicability of the present invention, the following example relates to *Streptococcus mutans* a bacteria commonly found in the human mouth and recognised as being involved in the development of dental carries. The examples also show the effect of different chain lengths of peptide.

Antimicrobial activity was determined by culturing cells of *Streptococcus mutans* NCTC10449 in broth, either in the absence of the peptide or in the presence of a polyarginine peptide of specified molecular weight.

When present, the peptide was present at a total concentration of 1.0 mg/ml, irrespective of molecular weight. Toxicity results, given in Table 5 below, are presented in terms of viable count in a sample of the broth at the indicated time.

TABLE 5

Effect of Molecular Weight

| Mol Wt: | Count (thousands) at indicated time (hours) | | | | | | | |
|---|---|---|---|---|---|---|---|---|
| | 0 | 0.5 | 1.0 | 1.5 | 2.0 | 2.5 | 3.0  3.5 | 4.0 |
| Control | 400 | 200 | 400 | 600 | 800 | 1000 | 1500 — | 2000 |
| 5–15 kD | 100 | 100 | 200 | 300 | 100 | 90 | 60 — | 40 |
| 15–70 kD | 100 | 100 | 100 | 80 | 40 | 20 | 14 — | 7 |
| 70–150 kD | 200 | 100 | 90 | 70 | 35 | 15 | 10 — | 2.4 |

From table 5 it can be seen that while the control sample exhibited exponential growth, all the samples which contained the poly arginine exhibited very low counts over the time course of the experiment. A high level of inhibition was obtained irrespective of the molecular weight of the peptide, although a general trend towards more marked inhibition at higher molecular weight is seen. It should be noted that at the higher molecular weights proportionally fewer peptide molecule are present in the sample.

Table 6, given below, presents data showing the effect of varying the level of an [Arg,Trp] peptide present using a constant molecular weight of peptide. In this example it can be seen that the growth of *Streptococcus mutans* NCTC10449 was inhibited by the presence of the peptide.

TABLE 6

Effect of Concentration

| Conc (mg/ml) | Count (millions) at indicated time (hours) | | | | | |
|---|---|---|---|---|---|---|
| | 0 | 0.5 | 1.0 | 1.5 | 2.0 | 2.5 |
| Control | 3.2 | 1.7 | 1.6 | 2 | 5.3 | 74 |
| 0.05 | 1.2 | 1.1 | 1.3 | 2 | 48 | 40 |
| 0.25 | 1.9 | 1.7 | 1.4 | 1.8 | 3.4 | 3.7 |
| 0.50 | 1.8 | 1.7 | 1.8 | 3.4 | 3.2 | 3.6 |
| 1.00 | 1.8 | 1.9 | 1.4 | 3 | 4 | 3.6 |

Table 7 presents data showing the effect of varying the level of an [Lys,Trp] peptide present using a constant molecular weight of peptide. In this example it can be seen that the growth of S. mutans NCTC10449 was inhibited by the presence of the peptide.

TABLE 7

Effect of Concentration

| Conc (mg/ml) | Count (millions) at indicated time (hours) | | | | | | | | |
|---|---|---|---|---|---|---|---|---|---|
| | 0 | 0.5 | 1.0 | 1.5 | 2.0 | 2.5 | 3.0 | 3.5 | 400 |
| Control | 30 | 540 | 530 | | 200 | | 460 | | 400 |
| 0.05 | 28 | 15 | 19 | | 26 | | 36 | | 140 |
| 0.25 | 35 | 12 | 18 | | 30 | | 28 | | 17 |
| 0.50 | 29 | 12 | 15 | | 40 | | 28 | | 12 |
| 1.00 | 28 | 13 | 14 | | 12 | | 4.8 | | 1.2 |

Example 4

Table 8 shows the inhibitory effect of the peptides according to the present invention on growth of *Actinomyces viscous* T14V.

Data is presented for poly[arg,trp] and poly[lys,trp], showing the initial viable count (millions) and the final viable count (millions) after four hours of incubation in the presence of varying concentrations of the peptide.

TABLE 8

Effect on *A. viscous* T14V

| | count (thousands) | | | |
|---|---|---|---|---|
| | poly [arg, trp] | | poly [lys, trp] | |
| Conc (mg/ml) | init. | fin. | init. | fin. |
| Control | 310 | 1200 | 48 | 4000 |
| 0.05 | 220 | 270 | 26 | 3100 |
| 0.25 | 240 | 270 | 8 | 600 |
| 0.50 | 240 | 60 | 10 | 60 |
| 1.00 | 220 | 58 | 10 | 30 |

Example 5

Table 9 lists the minimal inhibitory concentrations (MIC) in mg/ml for several of the peptides, assessed against *E. coli* and *L. inocula*. The MIC was measured in PGY medium as follows. Overnight cultures of the tested micro-organisms in PGY medium were diluted to a starting inoculum level of 10000 CFU/ml in PGY medium. Measurement were performed in a Titerek [TM] plate, using serial dilutions of 2.5, 1.25, 0,625, 0.31, 0,155, 0.078, 0.039 and 0.02 mg/ml and comparisons against blank wells with sterile medium and controls without poly amino acids.

TABLE 9

| Peptide | MICS | |
|---|---|---|
| | MIC/*E. coli* | MIC/*L. innocua* |
| poly [arg, trp] | 1.250 | 0.625 |
| poly [lys, lys] | 0.3125 | 0.160 |
| poly [orn, orn] | 0.3125 | 0.3125 |

From these results it can be seen that the peptides are effective at relatively low concentrations.

I claim:

1. A method for disinfecting matter infected with bacteria, comprising: the step of treating said matter with an antibacterial composition comprising at least 1% by wt. of a surfactant and a pseudo-random synthetic peptide, having an α-amino bonding group, said peptide having a molecular weight of at least 5 kD and comprising at least 15% by number of residues of arginine, lysine, ornithine or a mixture thereof and at least 15% by number of residues of arginine, lysine, ornithine or a mixture thereof and a least 15% by number of residues of arginine, lysine, ornithine, phenylalanine, tyrosine, tryptophan or a mixture thereof, said peptide comprising no more than three different amino acid residues.

2. A method according to claim 1 wherein the peptide comprises a homopolymer of arginine, ornithine or lysine.

3. A method according to claim 1 wherein the peptide is selected from the group consisting of copolymers of lysine and phenylalanine, arginine and tryptophan and lysine and tryptophan.

4. A method according to claim 1 wherein the peptide comprises at most 5000 amino acid residues.

5. A method according to claim 1 wherein the composition comprises 0.001–10 wt. % of said antibacterial peptide.

6. A method for disinfecting matter infected with bacteria, comprising the step of treating said matter with a liquid or paste antibacterial composition comprising:

a) 0.001–0.1 wt. % of an alpha linked pseudo-random synthetic peptide having a molecular weight of at least 5 kD, and comprising at least 15% by number of residues of arginine, lysine, ornithine or a mixture thereof and at least 15% by number of residues of arginine, lysine, ornithine, phenylalanine, tyrosine, tryptophan or a mixture thereof, said peptide comprising no more than 3 different amino acid residues, b) 1–30 wt. % of an ethoxylated alcohol surfactant and, c) as the balance of the composition, a compatible aqueous medium.

7. A method for disinfecting the matter infected with bacteria comprising the step of treating said matter with a liquid or a paste antibacterial composition comprising:

a) 0.001 to 0.1 wt. % of an alpha linked pseudo random synthetic peptide selected from the group consisting of copolymers of lysine and phenylalanine, arginine and tryptophan and lysine and tryptophan, b) 1 to 30 wt. % of an ethoxylated alcohol surfactant, and c) as the balance of the composition, a compatible aqueous medium.

* * * * *